United States Patent [19]

Nason

[11] Patent Number: 4,803,048
[45] Date of Patent: Feb. 7, 1989

[54] LABORATORY KIT

[76] Inventor: Frederic L. Nason, 6830 Orion Ave., Van Nuys, Calif. 91406

[21] Appl. No.: 33,220

[22] Filed: Apr. 2, 1987

[51] Int. Cl.$^4$ .................. G01N 1/10; G01N 33/48
[52] U.S. Cl. .................................... 422/58; 422/61; 422/102; 436/66; 206/469; 206/569; 229/125.03
[58] Field of Search ............... 422/58, 61, 102; 206/469, 569; 436/808, 66, 67; 435/810; 229/43

[56] References Cited

U.S. PATENT DOCUMENTS

| | | | |
|---|---|---|---|
| 2,370,683 | 3/1945 | Palma | 422/61 |
| 3,464,832 | 9/1969 | Mullinix | 229/43 |
| 4,078,656 | 3/1978 | Crane et al. | 206/456 |
| 4,201,795 | 5/1980 | Yamanaka | 229/43 |
| 4,420,353 | 12/1983 | Levine | 422/61 |

Primary Examiner—Benoit Castel
Assistant Examiner—Jill Johnston
Attorney, Agent, or Firm—Kelly, Bauersfeld & Lowry

[57] ABSTRACT

A laboratory kit is provided with a tear-off cover portion designed to fold into a compact package for containing and/or transporting a biological specimen or the like. The laboratory kit comprises a lower tray of vacuum-formed plastic or the like and containing selected laboratory implements such as a swab, glass slide, etc. A lightweight cover of paperboard or the like is affixed to and closes the tray. A tear-off portion of the cover is removable along perforated lines to open the tray and expose the implements therein for use, after which the tear-off portion is foldable along preformed score lines to form a compact package for containing a biological specimen or the like.

18 Claims, 2 Drawing Sheets

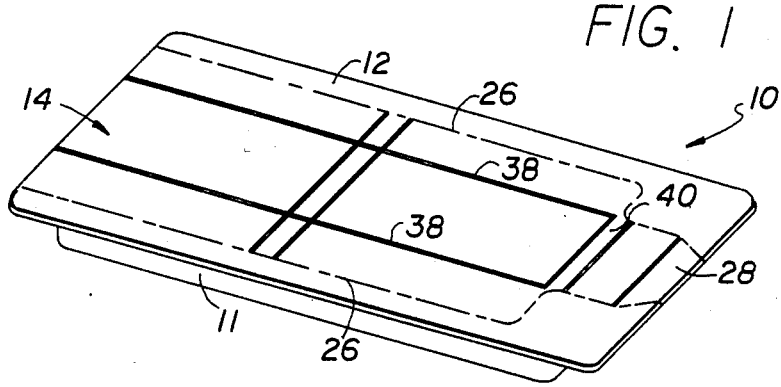
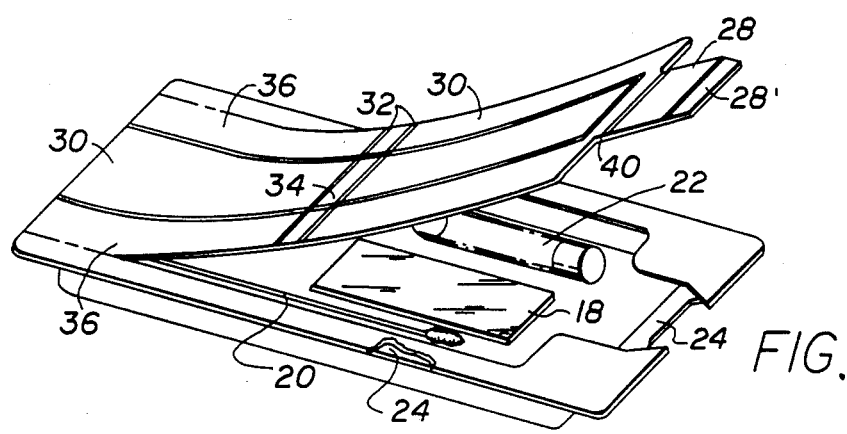
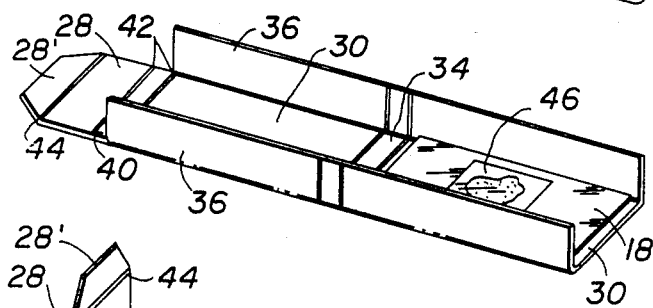
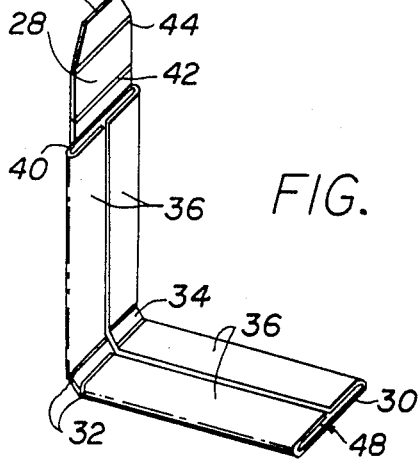
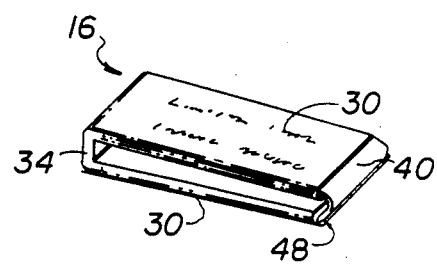

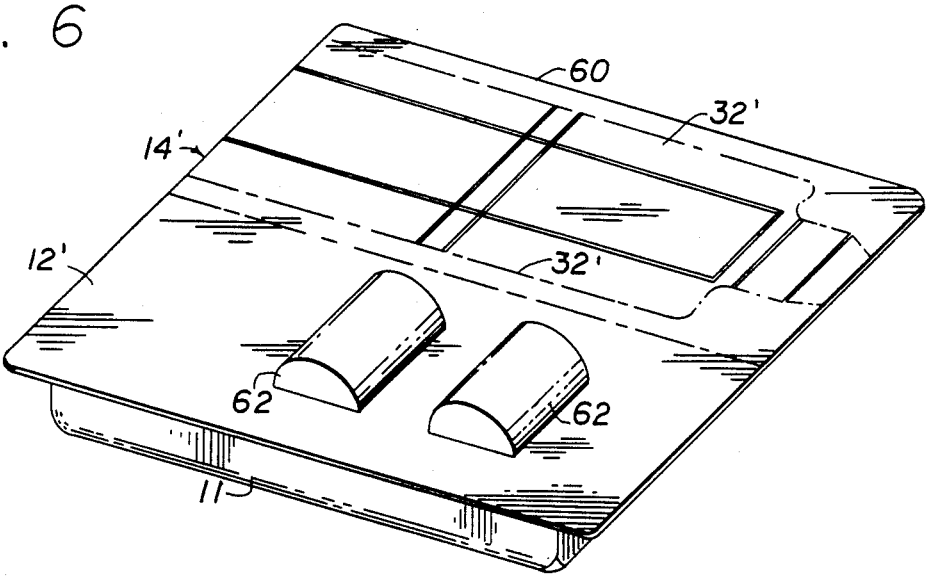
FIG. 6
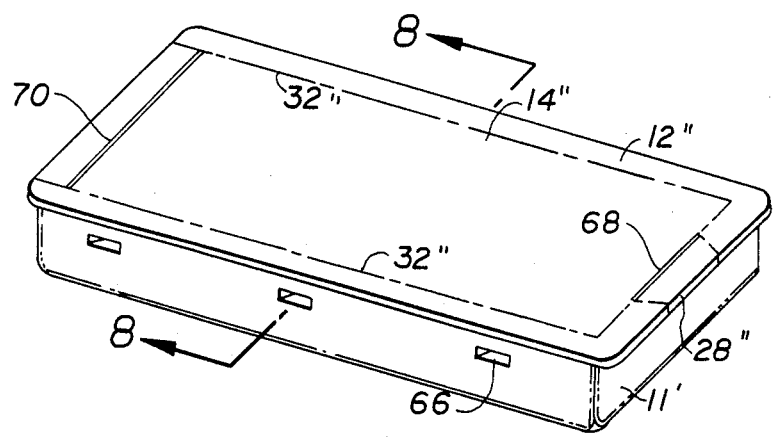
FIG. 7
FIG. 8
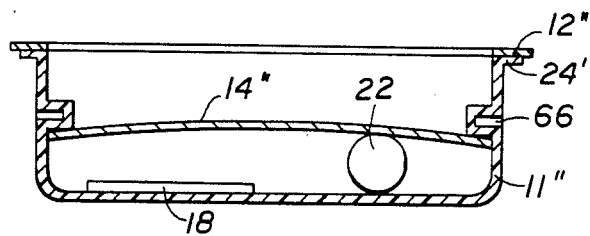

LABORATORY KIT

BACKGROUND OF THE INVENTION

This invention relates generally to laboratory kits particularly of the disposable type for use in the performance of a single laboratory procedure such as the collection of a biological specimen. More specifically, this invention relates to an improved laboratory kit having a tear-off cover portion designed for subsequent use as a compact package for containing and/or transporting a laboratory specimen.

Prepackaged laboratory kits are well known in the art for use in performing a wide variety of laboratory procedures. More specifically, prepackaged laboratory kits are widely used throughout the medical arts to facilitate a wide range of medical procedures, particulary the collection of patient biological specimens which are then transported to a medical laboratory for analysis. The test kit typically comprises a relatively lightweight and presterilized, if required, package containing one or more laboratory implements such as a glass slide, test tube, swab, spatula, reagent, or the like, with the particular implements being selected according to the specimen to be collected or other procedure to be performed. When performance of a test is desired, the kit is opened for easy access to the implements therein. when the test procedure is completed, the kit including the package and its contents are typically discarded.

When biological specimens and the like are collected using laboratory kits of the above-described general type, the specimen is normally placed upon a glass slide or other compact receptacle which is then transported to a laboratory facility for analysis. In this regard, there has existed a need for a compact container or package smaller than the laboratory kit but capable of protecting the slide or other receptacle to prevent glass breakage and further to prevent undesired human contact with the collected specimen. To this end, some test kits have been proposed to include packages designed to fold to a reduced size configuration to contain a glass slide and specimen thereon. See, for example, U.S. Pat. No. 4,078,656.

The present invention provides further improvements in such laboratory kits. More specifically, the present invention provides an economical kit designed for high volume production and safe containment of kit implements, with a portion of the kit being separable therefrom and forming a compact package for safe transport of a specimen or the like to a laboratory.

SUMMARY OF THE INVENTION

In accordance with the invention, an improved laboratory kit is provided with a tear-off cover portion forming a secondary and highly compact package for containing a collected biological specimen or the like. The tear-off cover portion is initially mounted upon and closes a lower kit tray within which selected test implements and instructions and the like are contained. When a test procedure is to be performed, the tear-off cover portion is separated from the remainder of the cover to permit implement access. When the procedure is completed, the tear-off cover portion is folded quickly and easily along preformed score lines to form a compact package containing the collected specimen, for example, upon a glass slide or the like.

In one preferred form of the invention, the kit tray is formed from a lightweight material such as vacuum formed plastic to have an upwardly presented peripheral lip. When the tray is packaged with the desired contents, the cover of lightweight paperboard or the like is placed over the tray and affixed to the lip by a suitable adhesive or the like. If desired, the entire kit as assembled, including the contents, may be sterilized as a unit.

The closed kit is opened by removing a portion of the cover along preformed perforated lines. Such removal is facilitated by forming the tear-off portion with a tongue at one end projecting beyond one end of the tray. The separated cover portion incorporates a plurality of preformed score lines for easy, accurate folding into the desired compact package.

In one alternative form of the invention, the cover for the tray includes a side portion or flap overhanging one side of the tray when said cover is mounted on the tray, wherein this side flap includes the tear-off cover portion. In another alternative form, the tear-off portion can be used without folding to reclose the tray. In this latter form, the tear-off portion can be pressed downwardly into the tray beyond relatively short indented tabs formed in the tray side walls. The tabs releasably lock the tear-off portion in place reclosing the tray.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating an improved laboratory kit embodying the novel features of the invention;

FIG. 2 is a perspective view illustrating the laboratory kit of FIG. 1 with a tear-off cover portion in a partially removed condition;

FIG. 3 is a perspective view illustrating the tear-off cover portion in a partially folded condition and encasing a glass slide or the like;

FIG. 4 is a perspective view illustrating the tear-off cover portion in a further folded condition;

FIG. 5 is another perspective view illustrating the tear-off cover portion folded into the form of a compact package;

FIG. 6 is a perspective view of one alternative form of the invention;

FIG. 7 is a perspective view of another alternative form of the invention; and

FIG. 8 is a transverse vertical sectional view taken generally along the line 8—8 of FIG. 7, and showing a tear-off cover portion used to reclose a tray.

DETAILED DESCRIPTION OF THE PREFERRED EMBODIMENTS

As shown in the exemplary drawings, a laboratory kit referred to generally by the reference numeral 10 is provided to encase various laboratory implements required to perform a selected test or other procedure. The kit 10 includes a lightweight tray 11 with a cover 12 having a tear-off portion 14 for easy kit opening, wherein the tear-off cover portion 14 folds quickly and easily into a compact package 16 (FIG. 5) sized to contain a biological specimen supported, for example, on a glass laboratory slide 18 or the like.

The improved test kit 10 of the present invention provides a lightweight and economical container for carrying a wide range of laboratory implements for use in performing a wide range of procedures, such as the collection of biological specimens for analysis. For example, as depicted in FIG. 2, the kit 10 can sized and shaped to receive implements such as the glass slide 18, a swab 20, and a glass vial 22 or the like carrying a medical or other laboratory reagent. The particular contents of the kit 10 are selected for use in performing a selected test or other procedure, for example, obtaining a throat culture from a patient, after which the kit contents are typically discarded. In many instances, a portion of the kit such as the glass slide 18 bearing the collected specimen is transported to a laboratory for further examination. The tear-off cover portion 14 of the cover 12 provides a convenient folding package of compact size for safely containing and transporting the slide 18.

As shown in one preferred form in FIGS. 1 and 2, the tray 11 of the kit 10 has a generally rectangular configuration shaped to define a shallow receptacle for the kit components. The tray 11 can be formed economically and at a high production rate by forming the tray from a lightweight plastic which can be produced by a vacuum forming process or the like to the desired size and shape. As shown best in FIG. 2, the side and end walls of the tray 11 merge at their upper ends in an upwardly presented peripheral lip 24 lying generally in a horizontal plane.

The cover 12 comprises, in the preferred form, a lightweight paperboard or light cardboard sheet sized generally to overlie the tray 11 in conformance with the outermost edges of the peripheral lip 24. The cover 12 is suitably secured to the tray lip 24 by an adhesive or other suitable fastening means to close the tray and thereby retain the contents therein. If desired, the tray 11 and the cover 12 can be adapted to undergo sterilization subsequent to mounting of the cover 12 thereby also sterilizing the contents of the kit.

When it is desired to perform a test or other procedure using the contents of the tray 11, the tear-off portion 14 of the cover 12 is removable quickly and easily from the remainder of the cover to expose the contents for use. More specifically, as shown best in FIG. 2, one end of the cover 12 extends a short distance beyond the underlying tray lip 24 to permit easy manual grasping of the cover at that end. A central region of this projecting end of the cover 12 is defined between a pair of generally parallel perforation lines 26 extending inwardly to a position spaced slightly inboard relative to the tray. The perforated lines 26 then turn away from each other and extend respectively in laterally opposite directions to positions generally above the tray side walls before turning back to a generally parallel orientation extending to the opposite end of the cover. These perforated lines 26 thus define the tear-off cover portion 14 with a tongue 28 at one end of the kit wherein the tongue can be grasped easily and pulled upwardly to separate the tear-off portion from the remainder of the cover.

During a typical test procedure, a collected biological specimen or other specimen is placed upon the glass slide 18 or other substrate, frequently after or in association with specimen contact with a reagent. As is known in the art, the slide provides a structure for transporting the specimen to a laboratory for further analysis. According to the invention, the slide 18 can be wrapped quickly and easily into the tear-off cover portion 14, as shown in FIGS. 3–5. More specifically, the tear-off portion 14 is subdivided by a plurality of preformed score lines to facilitate folding thereof into the compact package 16 shown in FIG. 5. The remaining components of the kit can be discarded.

As shown in FIG. 3, the tear-off portion 14 of the cover includes a pair of generally rectangular base panels 30 positioned end to end and separated by a pair of parallel transverse score lines 32 defining an intermediate end flap 34. Side flaps 36 are also included to extend longitudinally along the base panels 30 and the end flap 34, wherein these side flaps 36 are bounded by a pair of longitudinally running score lines 38. A second end flap 40 is defined between a pair of parallel score lines 42 at the base of the tongue 28, with the remainder of the tongue providing a closure tab 28' defined at the distal end thereof by an additional score line 44.

The base panels 30 are sized and shaped to support the glass slide 18 or other appropriate substrate with a biological specimen or the like thereon. The slide is placed upon one of the base panels and a coverslip 46 may be placed over the specimen, if desired. The side flaps 36 are then folded upwardly about the score lines 36 and then folded over the base panels 30 and the intermediate end flap 34. One of the two base panels 30 is then folded over the other as viewed in FIG. 4, with the transverse central score lines 32 permitting such folding motion and placing the end flap 34 in a position closing one end of the compact package. The tongue 28 including the folding tip 28' is then folded into the slot 48 defined at the opposite end of the portion 14 between the base panel 30 and the folded-over side flaps 36. The second end flap 40 at the base of the tongue 28 is thereby positioned to close the second end of the folded, compact package 16, as viewed in FIG. 5. The resultant package 16 safely encases and protects the slide 18 for storage and/or transport, for example, to a laboratory for further analysis.

In one alternative form of the invention, as shown in FIG. 6, a modified cover 12' is secured onto the underlying tray 11, with a tear-off cover portion 14' formed as an enlarged side flap 60 at one side of the tray. In this version, the portion of the cover overlying the tray 11 can be shaped to include upwardly extending discontinuities, such as the semi-cylindrical protrusions 62 shown is FIG. 6. This portion of the cover can be torn from the tray to expose the tray contents when the kit is required for a test procedure. The side flap 60 includes perforated lines 32' shaped as described with respect to FIGS. 1 and 2 to define the tear-off portion 14', which in turn is scored as previously described for easy folding to form the compact package 16 as shown in FIG. 5.

In another alternative form of the invention, as viewed in FIGS. 7 and 8, a further modified cover 12" is secured by an adhesive or the like onto the peripheral lip 24' of a modified tray 11'. In this embodiment, the tray 11' further includes a plurality of relatively short indented tabs 66 formed at spaced portions along the side walls of the tray. The cover 12" incorporates a modified tear-off portion 14" defined by generally parallel perforated lines 32" running along the tray side walls at the inboard sides thereof. At one end of the tray, these perforated lines 32" turn toward each other to run generally along the inboard side of the underlying end wall and terminate at the opposite margins of a longitudinally protruding tongue 28".

The tear-off cover portion 14" is separated easily to open the kit by pulling upwardly on the tongue 28".

With the kit open, the desired procedure can be performed. At the conclusion of the procedure, however, the kit is reclosed by pressing the tear-off portion 14" downwardly beyond the indented tabs 66, as viewed in FIG. 8, to retain selected contents of the kit therein. A score line 68 at the base of the tongue 28" and a second score line 70 near the opposite end of the portion 14" facilitate such downward displacement without interfering with the tray end walls.

The improved laboratory kit of the present invention thus provides a relatively simple and economical apparatus for containing the necessary implements to perform a wide variety of tests or procedures. The kit is opened quickly and easily, and a tear-off portion of the kit cover provides a simple structure for use in the transport of a collected specimen or the like to a laboratory for further testing.

A variety of further modifications and improvements to the laboratory kit described herein are believed to be apparent to those skilled in the art. Accordingly, no limitations on the invention are intended by way of the description herein, except as set forth in the appended claims.

What is claimed is:

1. A laboratory kit, comprising:
   at least one laboratory implement;
   a tray defining an upwardly open receptacle for receiving and storing said implement for use in performing a laboratory procedure; and
   a cover affixed to said tray for closing said tray and preventing access to the implement therein, said cover including a tear-off portion separable from said tray to open the tray and expose the implement therein for use in performing the laboratory procedure, said tear-off portion having a plurality of score lines preformed therein and being foldable along said score lines to form a relatively compact package for receiving and protecting the implement subsequent to performance of the laboratory procedure.

2. The kit of claim 1 wherein said tray comprises a lightweight vacuum-formed plastic.

3. The kit of claim 1 wherein said tray includes an upper peripheral lip, said cover being secured to said lip.

4. The kit of claim 1 wherein said cover comprises paperboard.

5. The kit of claim 1 wherein said cover includes preformed lines of perforation defining said tear-off portion.

6. The kit of claim 5 wherein said tear-off portion includes a tongue projecting beyond the underlying tray for easy manual grasping.

7. The kit of claim 1 wherein said tear-off portion of said cover comprises a side portion thereof projecting beyond one side of said tray.

8. The kit of claim 7 wherein said tray includes an upper peripheral lip, said cover being secured to said lip, said cover including a portion overlying said tray and having at least one upwardly extending discontinuity formed therein to extend substantially above said lip to accommodate the implement within said tray.

9. The kit of claim 1 wherein said tear-off portion is defined within said cover by a pair of preformed perforated lines and includes a tongue at one end thereof for easy manual grasping to separate said tear-off portion from the remainder of said cover, said plurality of preformed score lines defining lines of folding for said tear-off portion.

10. The kit of claim 9 wherein said tear-off portion is subdivided by said score lines into a pair of generally rectangular base panels lying generally end to end and separated by an intermediate end flap defined between a pair of generally parallel score lines, a pair of side flaps running longitudinally along the sides of said base panels and said intermediate end flap, and a second end flap defined generally at the base of said tongue, said side flaps being foldable to overlie said base panels and said intermediate end flap, said base panels being thereupon foldable one over the other and said tongue being insertable into a slot defined between the base panel and side flaps at the opposite end of the tear-off portion to position said second end flap closing the end of said compact package opposite said intermediate end flap.

11. The kit of claim 10 wherein said implement comprises a slide for supporting a collected specimen seated upon one of said base panels with the side flaps in overlying relation thereto.

12. A laboratory kit for use in collecting biological specimens and the like, said kit comprising:
    at least one implement for use in a selected procedure to collect a selected specimen;
    a tray defining an upwardly open receptacle for receiving and supporting the kit implement; and
    a cover mounted upon said tray to close the tray against access to said implement, said cover including a tear-off portion defined between a pair of preformed perforated lines for tear-off removal from the remainder of said tray to expose the implement therein for use, said implement including a specimen supporting substrate;
    said tear-off portion being subdivided by a plurality of scorelines for folding into a compact package having a size and shape for receiving and supporting said substrate with the specimen thereon.

13. The kit of claim 12 wherein said cover comprises paperboard.

14. The kit of claim 12 wherein said tear-off portion includes a pair of base panels lying generally end to end and separated by an intermediate end flap defined between a pair of generally parallel score lines, said tear-off portion further including a tongue at one end thereof for easy manual grasping to separate said tear-off portion from the remainder of said cover, said tongue including a second end flap, said tear-off portion further including a pair of side flaps running longitudinally along the sides of said base panels and said intermediate end flap.

15. A laboratory kit, comprising:
    at least one laboratory implement;
    a tray defining an upwardly open receptacle for receiving and storing the implement for use in performing a laboratory procedure, said tray having upstanding walls with relatively short indented tabs formed therein; and
    cover mounted upon said tray for closing said tray against access to the implement therein, said cover including a tear-off portion separable from the remainder of said cover to expose the implement therein for use, said tear-off portion having a size and shape for pressing downwardly into said tray to a position beyond said tabs whereby said tabs releasably retain said tear-off portion in a position reclosing said tray.

16. The kit of claim 15 wherein said tear-off portion includes a tongue at one end thereof for easy manual grasping to separate said tear-off portion from the remainder of said cover.

17. The kit of claim 16 wherein said tear-off portion further includes a first score line generally at the base of said tongue to permit folding of said tongue when said tear-off portion is pressed into said tray.

18. The kit of claim 17 wherein said tear-off portion further includes a second score line spaced generally in parallel from the end of said tear-off portion opposite said tongue to permit folding of an adjacent region thereof when said tear-off portion is pressed into said tray.

* * * * *